United States Patent [19]

King et al.

[11] Patent Number: 5,575,796
[45] Date of Patent: Nov. 19, 1996

[54] UMBILICAL CORD CUTTER AND SAMPLER

[75] Inventors: Eric M. King, West Jordan; Ben D. Shirley, Salt Lake City, both of Utah

[73] Assignee: Utah Medical Products, Inc., Midvale, Utah

[21] Appl. No.: 443,357

[22] Filed: May 17, 1995

[51] Int. Cl.$^6$ .................................................. A61B 17/00
[52] U.S. Cl. ................................................ 606/120; 128/760
[58] Field of Search ............................... 606/119, 120, 606/121, 153, 159, 167, 172, 184, 185; 128/760

[56] References Cited

U.S. PATENT DOCUMENTS

| | | | |
|---|---|---|---|
| 640,517 | 1/1900 | Acheson | 606/120 X |
| 1,710,766 | 4/1929 | Dilworth . | |
| 1,843,652 | 2/1932 | Taylor . | |
| 2,052,870 | 9/1936 | Coco | 128/346 |
| 2,060,724 | 11/1936 | Carroll | 128/346 |
| 2,127,190 | 8/1938 | Solomon | 128/321 |
| 2,307,377 | 1/1943 | Riccardi | 128/346 |
| 2,366,424 | 1/1945 | Perry | 128/214 |
| 2,434,831 | 1/1948 | Brandenburg | 128/346 |
| 2,498,372 | 2/1950 | Kortlucke et al. | 128/346 |
| 2,524,337 | 10/1950 | Whittaker | 128/305 |
| 2,626,608 | 1/1953 | Garland | 128/346 |
| 2,796,867 | 6/1957 | Pearson | 128/346 |
| 3,016,056 | 1/1962 | Jacobs | 128/346 |
| 3,040,749 | 6/1962 | Payton | 128/346 |
| 3,106,919 | 10/1963 | Churchville | 128/346 |
| 3,150,666 | 9/1964 | Averbach | 128/326 |
| 3,166,071 | 1/1965 | Mayer | 606/120 |
| 3,171,184 | 3/1965 | Posse | 24/248 |
| 3,203,421 | 8/1965 | Bialick | 128/346 |
| 3,247,852 | 4/1966 | Schneider | 128/346 |
| 3,277,895 | 10/1966 | Johnson | 128/325 |
| 3,315,679 | 4/1967 | Sarracino | 128/346 |
| 3,323,208 | 6/1967 | Hurley, Jr. | 606/120 |
| 3,497,175 | 2/1970 | Koland | 251/9 |
| 3,561,448 | 2/1971 | Peternel | 128/334 |
| 3,631,858 | 1/1972 | Ersek et al. | 128/318 |
| 3,669,115 | 6/1972 | Melges | 128/305 |
| 3,687,131 | 8/1972 | Rayport et al. | 128/2 B |
| 3,705,586 | 12/1972 | Sarracino | 128/346 |
| 3,706,312 | 12/1972 | Melges | 128/305 |
| 3,807,406 | 4/1974 | Rafferty et al. | 128/318 |
| 3,825,012 | 7/1974 | Nicoll | 128/346 |
| 3,828,822 | 8/1974 | Witte | 138/45 |
| 3,854,482 | 12/1974 | Laugherty et al. | 606/120 |
| 3,916,908 | 11/1975 | Leveen | 128/346 |
| 3,980,086 | 9/1976 | Kletschka et al. | 128/318 |
| 4,026,294 | 5/1977 | Mattler | 128/305 |
| 4,112,944 | 9/1978 | Williams | 128/214 R |
| 4,128,326 | 12/1978 | Selak | 354/31 |
| 4,165,747 | 8/1979 | Bermant | 128/334 C |
| 4,191,359 | 3/1980 | Andersson et al. | 251/9 |
| 4,212,303 | 7/1980 | Nolan | 128/346 |
| 4,327,746 | 5/1982 | Feaster | 128/764 |
| 4,345,600 | 8/1982 | Rothfuss | 128/334 R |
| 4,387,489 | 6/1983 | Dudek | 24/133 |

(List continued on next page.)

FOREIGN PATENT DOCUMENTS

| | | |
|---|---|---|
| 425-627 | 2/1975 | U.S.S.R. . |
| WO92/16150 | 10/1992 | WIPO . |

*Primary Examiner*—Sam Rimell
*Attorney, Agent, or Firm*—Madson & Metcalf

[57] ABSTRACT

An apparatus for clamping, cutting, and collecting a blood sample from an umbilical cord is disclosed. The apparatus includes a housing for receiving and entrapping a section of umbilical cord. The housing is formed by a lid and a handle connected at a hinge. Upon closing the lid, the umbilical cord is clamped with a clamp removably connected to the housing. A slidable blade assembly cuts the umbilical cord using a slicing motion. A blood collection chamber located in the handle collects blood from the cut umbilical cord. A fluid passageway connects the blood collection chamber to one or more blood containers. An absorbent gasket surrounds the blood collection chamber in the handle for collecting and retaining excess blood that may exceed the capacity of the collection chamber. A placenta clamp is provided for gripping or clamping the placenta side of the umbilical cord after it has been cut.

31 Claims, 7 Drawing Sheets

U.S. PATENT DOCUMENTS

| | | | |
|---|---|---|---|
| 4,428,374 | 1/1984 | Auburn | 128/318 |
| 4,572,181 | 2/1986 | Mattler | 128/305 |
| 4,602,629 | 7/1986 | Schnirman | 128/305 |
| 4,616,801 | 10/1986 | Cewers et al. | 251/6 |
| 4,630,608 | 12/1986 | Arroyo | 128/335 |
| 4,644,953 | 2/1987 | Lahodny et al. | 128/305 |
| 4,648,401 | 3/1987 | Mattson | 128/305 |
| 4,662,371 | 5/1987 | Whipple et al. | 128/312 |
| 4,716,886 | 1/1988 | Schulman et al. | 128/305 |
| 4,773,431 | 9/1988 | Lodomirski | 128/769 |
| 4,781,188 | 11/1988 | Collins | 128/305 |
| 4,856,517 | 8/1989 | Collins et al. | 128/346 |
| 4,870,965 | 10/1989 | Jahanger | 128/318 |
| 4,895,276 | 1/1990 | Maldonado | 222/144.5 |
| 4,938,215 | 7/1990 | Schulman et al. | 606/120 |
| 4,970,052 | 11/1990 | Oberhardt et al. | 422/101 |
| 4,972,843 | 11/1990 | Brodén | 128/760 |
| 4,976,271 | 12/1990 | Blair | 128/764 |
| 4,980,297 | 12/1990 | Haynes et al. | 436/178 |
| 5,009,657 | 4/1991 | Cotey et al. | 606/120 |
| 5,127,915 | 7/1992 | Mattson | 606/120 |
| 5,178,624 | 1/1993 | Kyun | 606/120 |
| 5,190,556 | 3/1993 | Hessel | 606/120 |
| 5,342,328 | 8/1994 | Grossman et al. | 604/317 |
| 5,415,665 | 5/1995 | Hessel et al. | 606/120 |

UMBILICAL CORD CUTTER AND SAMPLER

BACKGROUND

1. Field of the Invention

The present invention relates to a device for cutting and clamping an umbilical cord and for collecting a blood sample from the umbilical cord.

2. Technology Review

The current process in the delivery of infants requires that the umbilical cord be clamped and cut shortly after the moment of birth. The function of the cord is the transmission of nutrients and oxygen between the mother and child through blood flowing in the cord. The cord is engorged with blood at birth when severed by the obstetrician to free the infant from the mother. It is often difficult to clamp and cut the cord at the moment of birth because of fluid present, including blood and amniotic fluid from the mother, making physician's gloved hands slippery.

Samples of the blood in the cord are commonly collected at birth for chemical and biological assay to determine if the newborn is subject to possible genetically transmitted diseases. Two common methods are used to collect cord blood samples. These methods include draining the blood from the cut umbilical cord directly into an open vial or extracting the blood directly from the cord using a syringe and needle.

The draining method often requires the cord segment to be hand "milked" by squeezing the cord such that blood in the segment flows toward the sample vial. This "milking" action causes the flow of many contaminants in addition to the desired blood into the vial. Such contaminants may affect the testing of the cord blood sample. As the complexity and sensitivity of the genetic tests increase, the absence of contamination in the sample becomes more important.

The extracting method requires using a syringe and needle to remove the blood directed from the cord. The needle is used to puncture the cord and the syringe is used to collect a blood sample. Care must be taken to prevent inadvertent needle sticks which can lead to blood exposure.

It will be appreciated that there is a need in the art for improved devices and methods of clamping and cutting the umbilical cord and for obtaining an uncontaminated cord blood sample.

Such devices and methods are disclosed herein.

SUMMARY OF THE INVENTION

The present invention discloses an apparatus for clamping, cutting, and collecting a blood sample from an umbilical cord. The apparatus includes a housing for receiving and entrapping a section of umbilical cord. In a currently preferred embodiment, the housing is formed by a lid and a handle connected at a hinge such that the lid may be moved from an open position to a closed position. The open position allows an umbilical cord to be inserted between the handle and the lid.

Upon closing the lid, the umbilical cord is clamped with a cord clamp removably connected to the housing. A large number of umbilical cord clamps are known in the art. In a currently preferred embodiment, the cord clamp is a one-piece living hinge design containing a self-aligning latch.

The housing contains a blade assembly for cutting the umbilical cord. The blade assembly includes a sharp blade, such as a standard razor blade, for cutting the umbilical cord. In a presently preferred embodiment, the blade assembly is slidably located in the lid and configured to slide at an angle less than 90° with respect to the blade surface to provide a slicing motion to cut the umbilical cord. The blade assembly includes means for releasing the cord clamp from the housing when the umbilical cord is cut. In a preferred embodiment, the clamp is released from the housing by a cam located on the blade assembly.

The handle forms a blood collection chamber. When the umbilical cord is cut, blood drains into the blood collection chamber. At the bottom of the blood collection chamber is a fluid passageway to one or more blood containers, such as standard vacuum tubes. An absorbent gasket preferably surrounds the blood collection chamber in the handle for collecting and retaining excess blood that may exceed the capacity of the collection chamber. The gasket also collects any blood that may remain in the chamber after the collecting process.

The apparatus of the present invention preferably includes a placenta clamp located in the housing having a surface for gripping or clamping the placenta side of the umbilical cord after it has been cut. A cord restraint, such as a plurality of angled needles, is optionally provided to penetrate the umbilical cord when a pulling force is made against the umbilical cord. The placenta clamp and the cord restraint facilitate delivery of the placenta. In a currently preferred embodiment, the placenta clamp and the cord restraint are located in the lid. The placenta clamp preferably includes ratchet teeth to maintain clamping action of the placenta clamp against the umbilical cord. In a preferred embodiment, engaging the placenta clamp breaks a valve in the blood collection chamber creating a fluid passageway between the blood collection chamber and one or more vacuum tubes used to retain the blood samples. Just like the blade assembly, the placenta clamp is preferably configured to slide at an angle less than 90° with respect to the clamp surface.

DESCRIPTION OF THE DRAWINGS

A more particular description of the invention briefly described above will be rendered by reference to the appended drawings. These drawings only provide information concerning typical embodiments of the invention and are not therefore to be considered limiting of its scope. The invention will be described and explained with additional specificity and detail through the use of the accompanying drawings, in which.

DETAILED DESCRIPTION OF THE PREFERRED EMBODIMENTS

Figure 1:
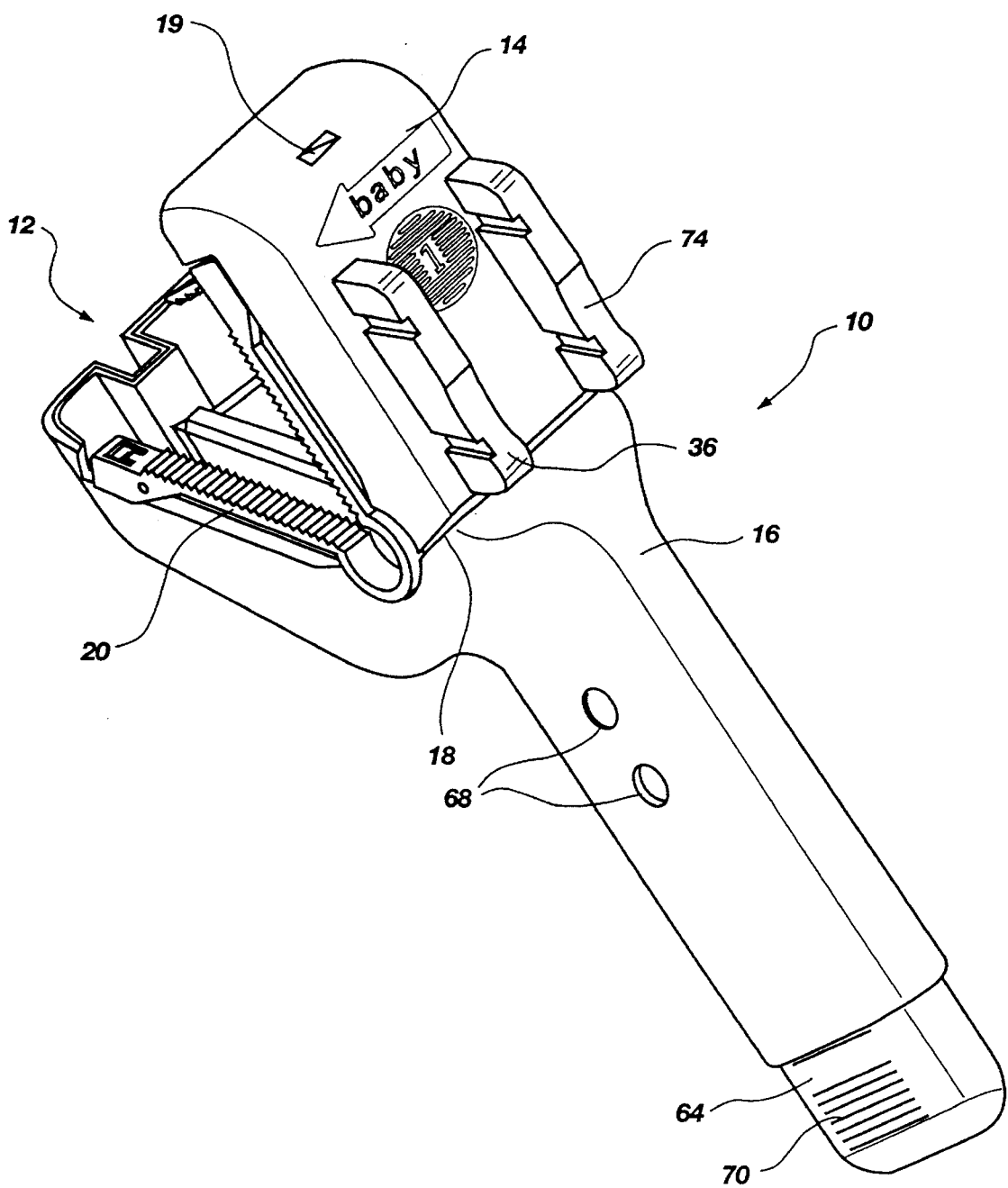
FIG. 1 is a perspective view of an umbilical cord clamping, cutting, and blood sampling device within the scope of the present invention.
Figure 2:
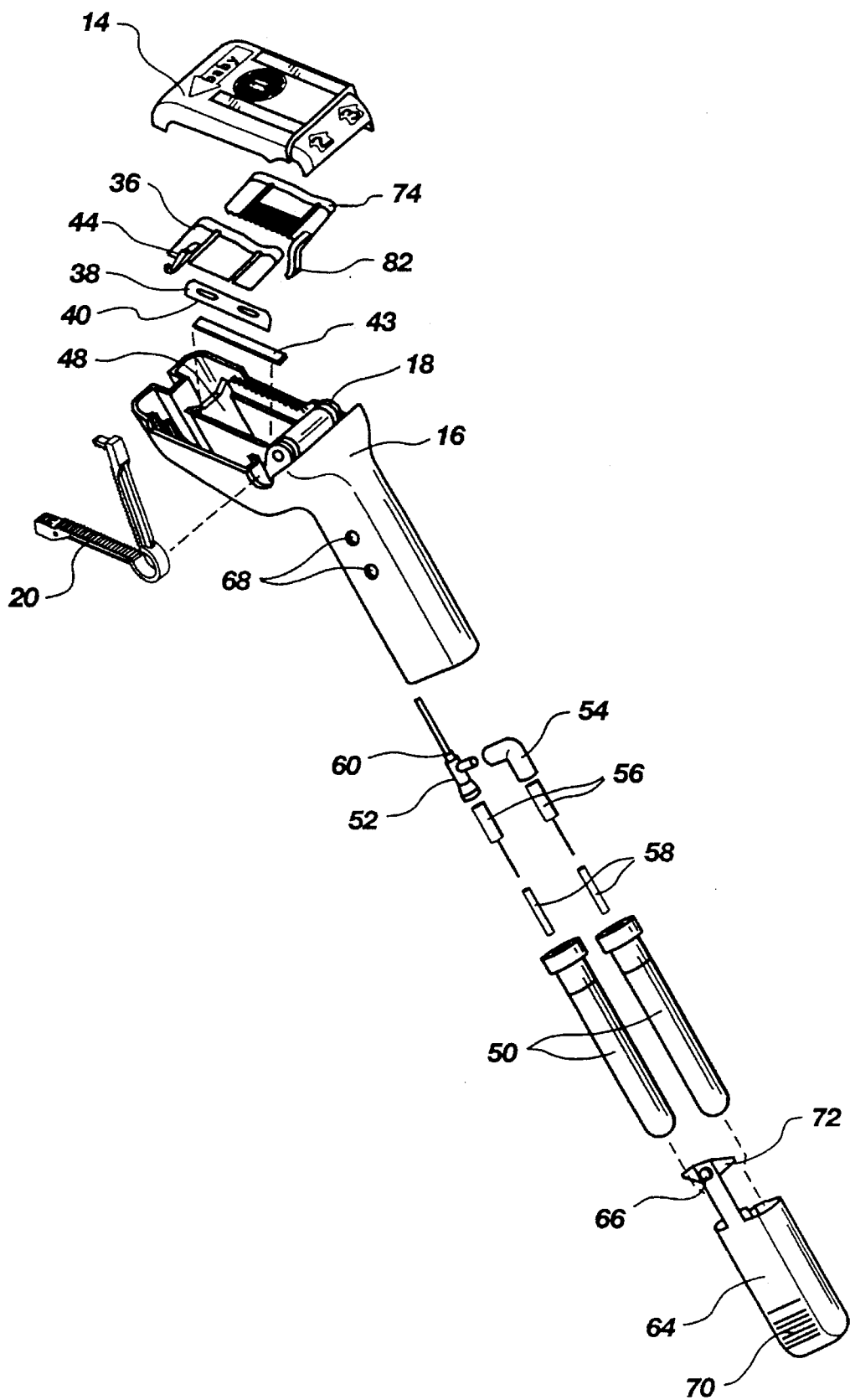
FIG. 2 is an exploded perspective view of the device shown in FIG. 1.
Figure 3:
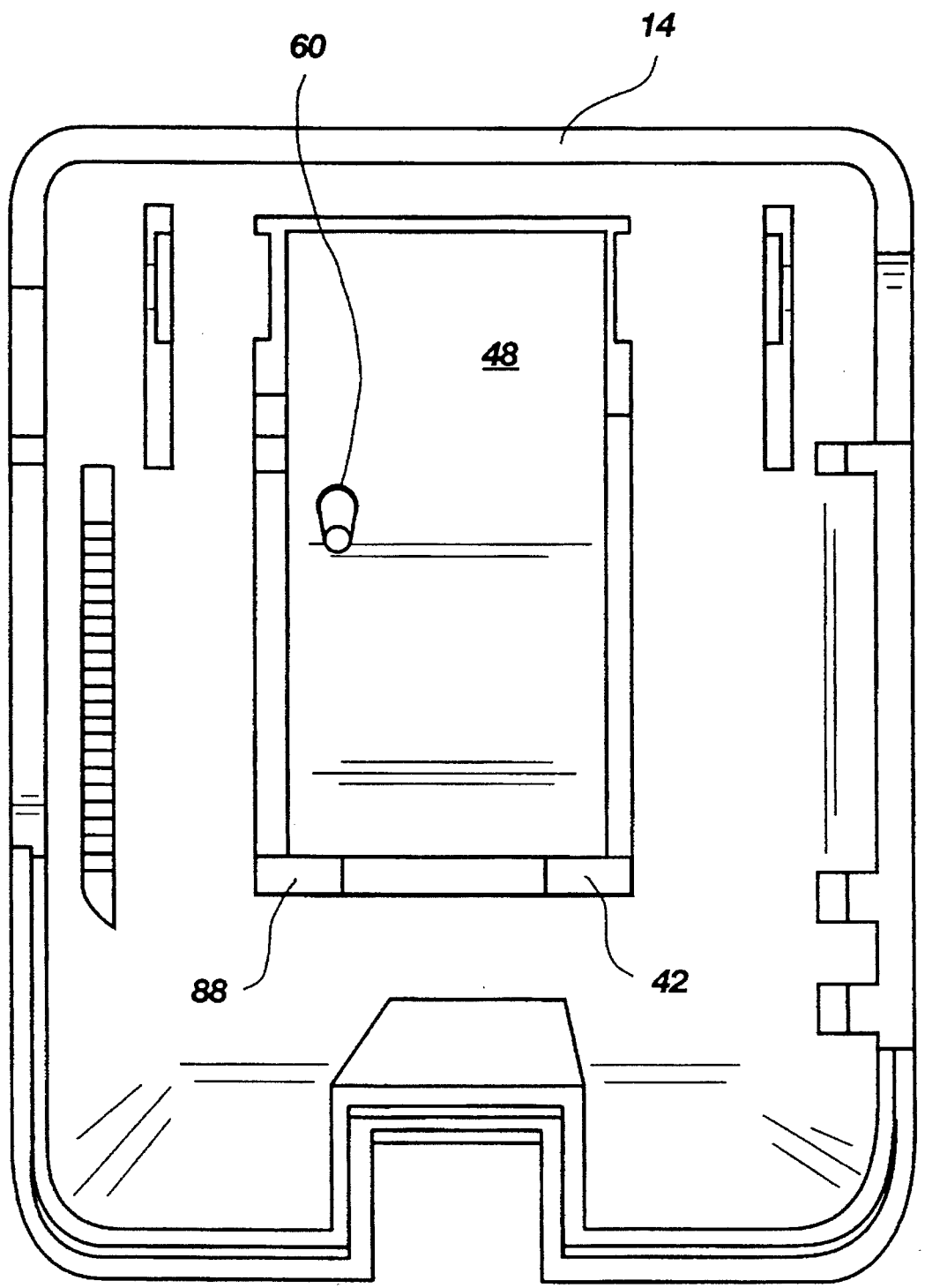
FIG. 3 is a top view of interior of the handle portion of the device shown in FIG. 1.

Reference is now made to the figures wherein like parts are referred to by like numerals throughout. With particular reference to FIG. 1, an apparatus for clamping, cutting, and collecting a blood sample from an umbilical cord according to the present invention is generally designated at 10. The component parts of apparatus 10 are shown in an exploded perspective view in FIG. 2. The apparatus 10 includes a housing 12 for receiving and entrapping a section of umbilical cord (not shown). The housing 12 is formed by a lid 14 and a handle 16 connected at a hinge 18 such that the lid 14 may be moved from an open position to a closed position. The open position allows an umbilical cord to be inserted between the lid 14 and handle 16. A latch 19 located on the front of the lid 14 locks the lid shut when it is closed. The lid 14 and handle 16 are preferably molded of polymeric materials which permit easy snap-fit assembly. A currently preferred polymeric material used to mold the lid 14 and handle 16 is ABS plastic.

The action of closing the lid 14 upon an umbilical cord causes the cord to be clamped with a cord clamp 20. The umbilical cord clamp 20 is preferably removably connected to the housing 12. A large number of umbilical cord clamps are known in the art, any number of which could be adapted for use in the present invention. In a currently preferred embodiment, the clamp 20 is a one-piece living hinge design containing a self-aligning latch. Clamp 20 is preferably molded of a polymeric material having sufficient strength and elasticity to provide the living hinge functionality. Isoplast is a currently preferred polymeric material suitable for molding the clamp 20.

Figure 6:
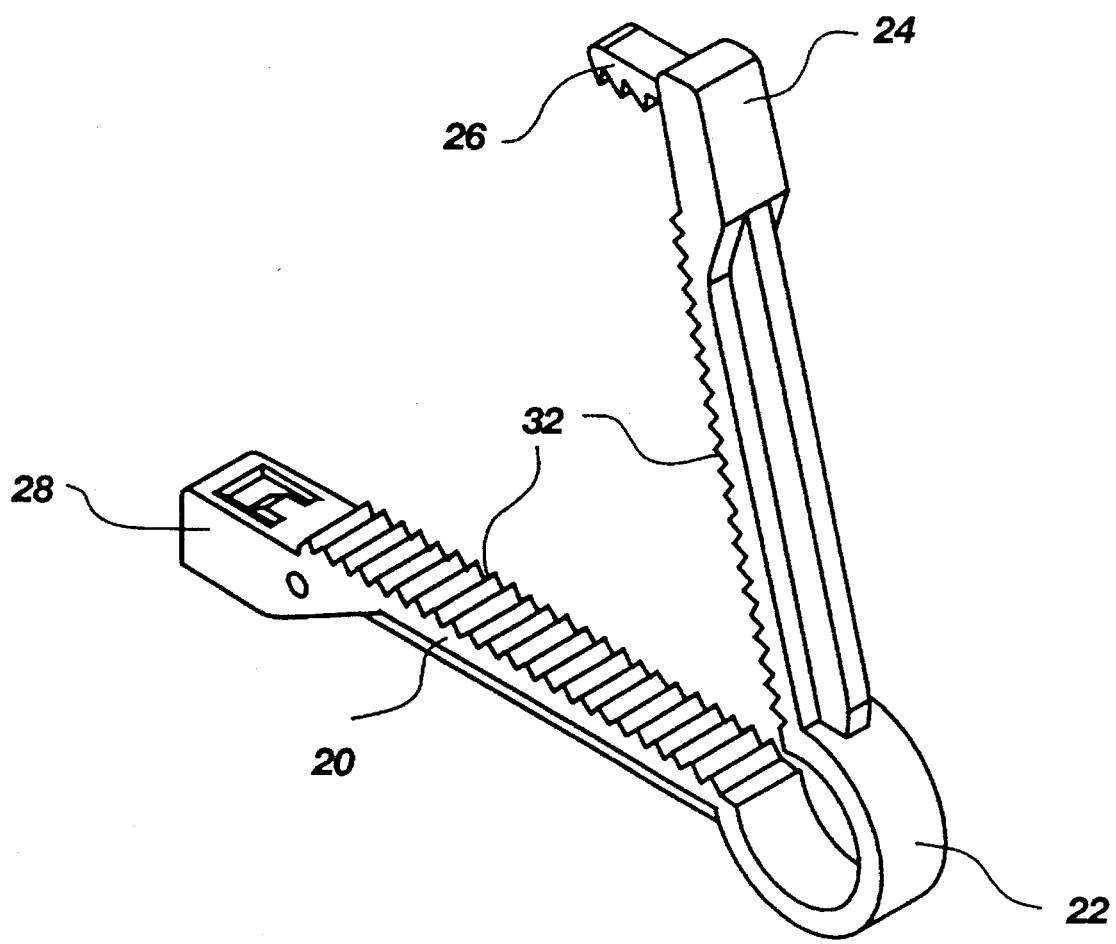
FIG. 6 is a perspective view of an umbilical cord clamp capable of use in the device of the present invention.

A currently preferred clamp design is shown in FIG. 6, the umbilical cord clamp 20 is molded at a 65° to 70° angle. The clamp 20 includes a living hinge 22 to keep the hinge open until it is forcibly closed. Because the hinge 18 of lid 14 and handle 16 can only open to about 55°, the clamp 20 produces a constant retention force against the lid 14 and handle 16. The male latch member 24 includes a ratchet surface 26 designed to engage female latch member 28. The ratchet surface 26 provides the clamp 20 with several locking positions. The ratchet surface 26 permits the cord clamp 20 to be used with umbilical cords that are either thin or thick. In addition, the cord clamp 20 is designed to be easily and securely closed with a minimum of effort by the medical practitioner. Once the latch members 24 and 28 have engaged each other, the clamp 20 cannot be unlatched. Removal of the clamp 20 from the umbilical cord requires cutting of the living hinge 22. As shown in FIG. 6, the clamp 20 includes a rough or irregularly shaped clamping surface 32 to firmly hold the umbilical cord within the clamp.

Figures 4, 5:
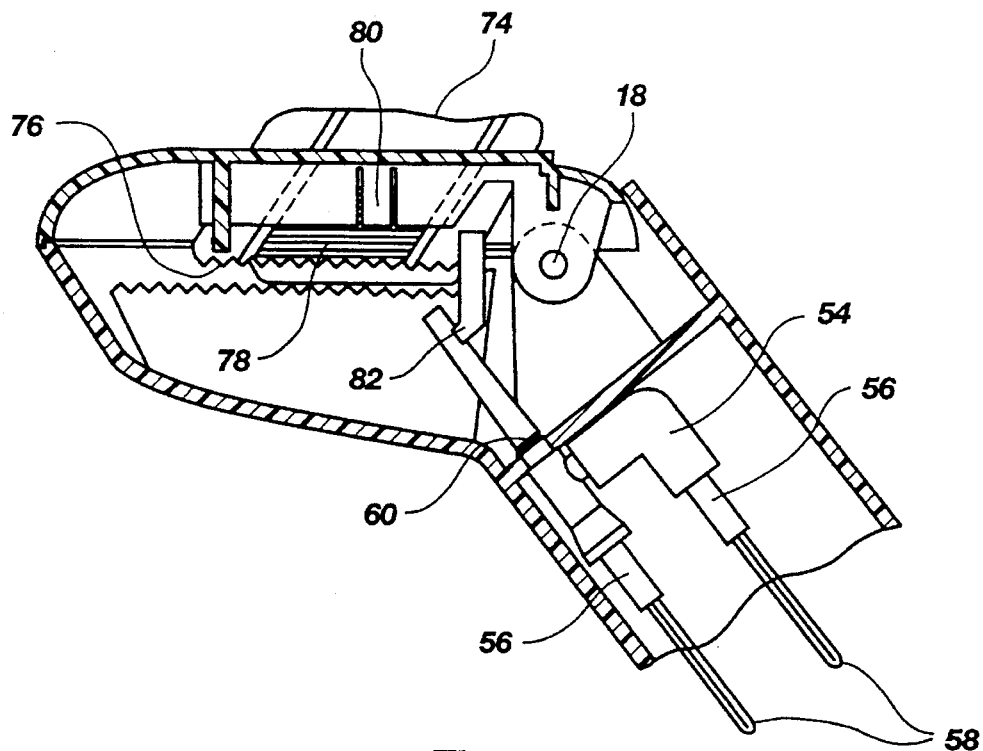
FIG. 4 is a cross-sectional side view of an umbilical cord clamping, cutting, and blood sampling device showing a placenta clamp, blood collection chamber, and a fluid passageway between the blood collection chamber and a blood container.
FIG. 5 is a cross-sectional side view of the device shown in FIG. 4 showing the sliding action of a blade assembly according to the present invention.

Referring again to FIGS. 1 and 2, the housing 12 contains a blade assembly 36 for cutting the umbilical cord. Attached to the blade assembly 36 is a sharp blade 38, such as a standard stainless steel razor blade, for cutting the umbilical cord. The sharp blade 38 includes a blade surface 40. In a presently preferred embodiment, the blade assembly 36 is slidably located in the lid 14 and configured to slide at an angle less than 90°, and preferably about 60°, with respect to the blade surface 40 to provide a slicing motion to cut the umbilical cord. FIG. 5 shows a cross-sectional view of the blade surface 40A prior to cutting the umbilical cord and the blade surface 40B, shown in phantom lines, in its position after cutting the umbilical cord. The top of the blade assembly 36 is preferably textured to prevent the thumb from slipping during actuation.

Figure 7:
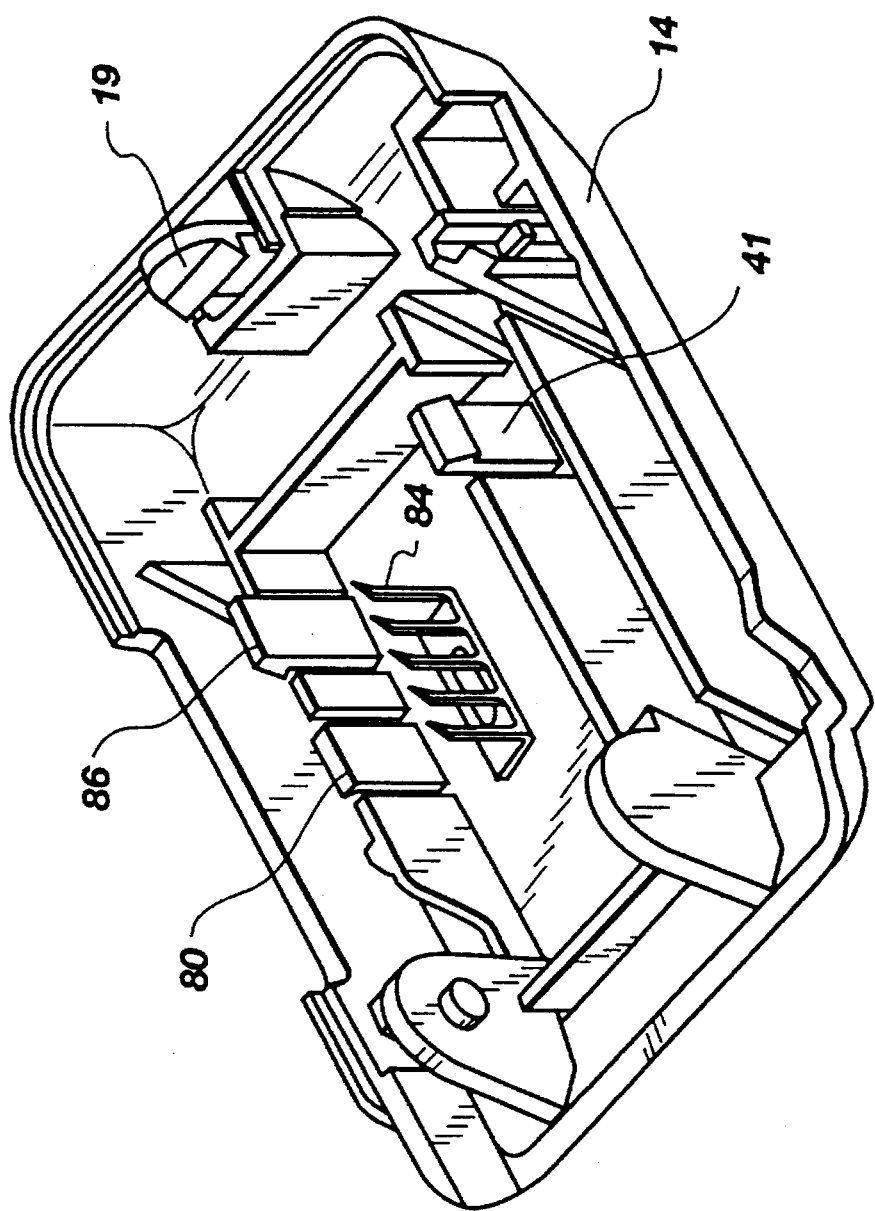
FIG. 7 is a perspective view of one possible lid interior configuration.
Figure 8:
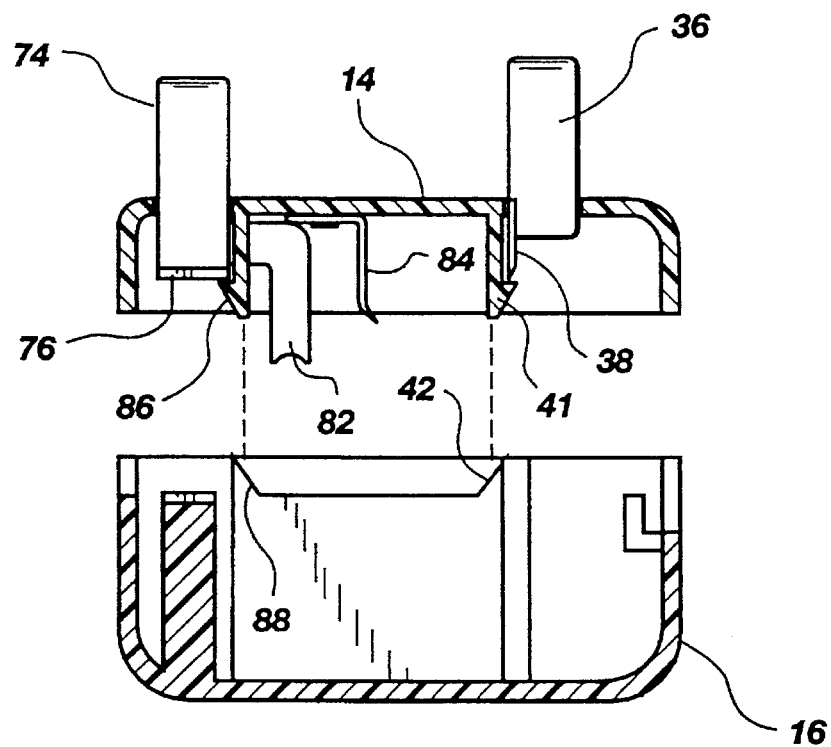
FIG. 8 is a side, cross-sectional view of the lid and handle illustrating one possible configuration of the placenta clamp and blade assembly safety locks.

An interlock system is preferably provided in the housing 14 to prevent the blade assembly 36 from engaging until the lid 14 is closed. In embodiment illustrated in FIGS. 7 and 8, a blade safety lock 41 prevents the blade assembly 36 from engaging when the lid 14 is open. As shown in FIG. 8, the handle 16 preferably includes an angled ramp surface 42 which causes the safety lock 41 to deflect when the lid 14 is closed. With the safety lock 41 deflected, the blade assembly 36 is free to be pressed downward to cut the umbilical cord and to release the cord clamp.

An anvil 43 provides a surface for the blade 38 to cut against. The blade surface 40 is buried in the anvil 43 at the end of the cutting stroke. A wide variety of materials can be used for the anvil 43, including synthetic polymeric materials. Silicone rubber is a currently preferred anvil material.

The blade assembly 36 preferably includes means for releasing the clamp 20 from the housing 12 when the umbilical cord is cut. In the illustrated embodiment, the clamp 20 is released from the housing 12 by a cam 44 located on the side of the blade assembly 36. When the blade assembly 36 is actuated, the cam pushes the cord clamp 20 out of the housing 12.

Figure 9:
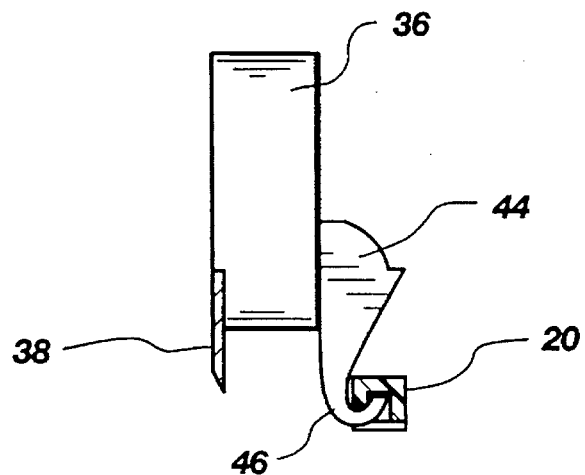
FIG. 9 is a side view blade assembly showing a clamp hook for retaining the umbilical cord clamp.

The blade assembly 36 preferably includes a cord clamp retainer. Because the cord clamp 20 is closed when the 14 lid is closed, it is desirable to keep the cord clamp affixed to the housing 12 until the cord clamp 20 has been closed around the umbilical cord and released from the housing when the umbilical cord is cut. The embodiment illustrated in FIG. 9 shows a clamp hook 46 for holding the cord clamp 20 to the housing 12. When the blade assembly 36 is actuated, the cam pushes the cord clamp 20 out of the housing 12 and at the same time the camming action releases the cord clamp from hook 46.

The handle 16 forms a blood collection chamber 48. When the umbilical cord is cut, blood drains into the blood collection chamber 48. At the bottom of the blood collection chamber 48 is a fluid passageway to a pair of standard vacuum tubes 50 used in the medical industry for collecting blood samples. The fluid passageway shown in FIGS. 2 and 4 includes a valve tee 52, an elbow 54, a pair of vacuum tube needles 56 each with a rubber needle cover 58.

The elbow 54 is connected to the valve tee 52 to provide a fluid passageway to a second vacuum tube. The elbow 54 is preferably designed with a standard female lure lock taper for a press fit onto the valve tee 52. The elbow is preferably constructed of a polymeric material such as ABS plastic. A pair of standard vacuum tube needles 56 are attached to the valve tee 52 and to the elbow 54. The needle covers 58 are commercially available. The needle covers provide additional safety protection from inadvertent needle sticks and prevent blood from draining out of the needles.

The valve tee 52 is preferably designed with a standard male luer lock taper for easy press fit assembly into the handle 16. A molded notch 60 at the base of the valve tee 52 permits the valve tee 52 to be broken (described in greater detail below), thereby opening the fluid passageway between the blood collection chamber 48 and the vacuum tubes 50. The valve tee 52 is preferably constructed of a polymeric material such as polystyrene.

The vacuum tubes are preferably housed within a sheath 64. A button 66 located on the side of the sheath 64 locks into one of two holes 68 in the handle 16. The button 66 and holes 68 provide a means of keeping the vacuum tubes 50 off the needles 56 during manufacture and shipping and on the needles 56 during use. The button 66 and holes 68 also permit the user to readily determine the location of the sheath 64 within the handle 12 and whether the vacuum tubes 50 have penetrated the vacuum tube needles 56. Raised ribs 70 located at the bottom of the sheath 64 allow the sheath to be easily removed from the handle 16. A pair of living hinge flaps 72 located at the top of the sheath 64 retains the vacuum tubes 50 within the sheath 64. The flaps 72 are configured to bend over the top of the vacuum tubes 50 to facilitate removal of the vacuum tubes from the vacuum tube needles 56. Once the sheath 64 is removed from the handle 16, the flaps 72 can be easily bent out of the way to allow removal of the vacuum tubes 50. The sheath is preferably molded out of a polymeric material, such as polypropylene.

An absorbent gasket (not shown) preferably surrounds the blood collection chamber 48 in the handle 16 for collecting and retaining excess blood that may exceed the capacity of the collection chamber 48. The gasket also collects any blood that may remain in the chamber after the collecting process. Suitable gasket material is commercially available in the medical industry. One currently preferred absorbent gasket material is bonded cellulose acetate.

The apparatus 10 preferably includes a placenta clamp 74 located in the housing having a clamp surface 76 for gripping or clamping the placenta side of the umbilical cord after it has been cut. The placenta clamp 74 facilitates delivery of the placenta. In the illustrated embodiment, the placenta clamp 74 is located in a slot within the lid 14. The placenta clamp 74 preferably includes ratchet teeth 78 to maintain clamping action of the placenta clamp against the umbilical cord. The ratchet teeth 78 engage a slot ratchet 80 in the lid. Just like the blade assembly 36, the placenta clamp 74 is preferably configured to slide at an angle less than 90° with respect to the clamp surface 76. A valve break off arm 82 extends downward from the side of the placenta clamp 74 to break the valve tee 52 when the placenta clamp 74 is engaged.

An umbilical cord restraint 84 is preferably provided to assist the placenta clamp in gripping and retaining the umbilical cord. In the illustrated embodiment, the cord restraint 84, located on the underside of lid 14, includes a plurality of needle-like or teeth-like projections which are sharp enough to penetrate the umbilical cord when the lid 14 is closed.

An interlock system is optionally provided in the housing 14 to prevent the placenta clamp 74 from engaging until the lid 14 is closed. In embodiment illustrated in FIGS. 7 and 8, a placenta clamp safety lock 86 prevents the placenta clamp 74 from engaging when the lid 14 is open. As shown in FIG. 8, the handle 16 preferably includes an angled ramp surface 88 which causes the safety lock 86 to deflect when the lid 14 is closed. With the safety lock 86 deflected, the placenta clamp 74 is free to be pressed downward to retain the umbilical cord and to facilitate delivery of the placenta.

The present invention may optionally be constructed of materials which permit the apparatus to be disposable. Current technology permits one skilled in the art to construct the apparatus entirely from non-metallic parts. For instance, the sharp blade 38 and cord restraint 84 can be manufactured from commercially available glass filled material. Similarly, plastic vacuum tubes and vacuum tube needles are commercially available. With the entire apparatus manufactured from nonmetallic parts, the apparatus can be easily incinerated leaving no metallic residue.

The apparatus of the present invention is prepared for use by pressing the sheath 64 containing the vacuum tubes 50 further into the handle 16 such that the vacuum tube needles 58 penetrate the vacuum tubes 50. An umbilical cord is then placed within the housing, and the lid 14 is closed upon the handle 16. The closing action of the lid causes the two latch members 24 and 28 of clamp 20 to engage thereby clamping the umbilical cord. The user then presses the blade assembly 36 such that it slices the umbilical cord and releases the clamp 20 from the apparatus. Blood from the freshly cut umbilical cord quickly fills the blood collection chamber 48. The user then presses the placenta clamp 74 which breaks the valve tee 52 releasing the vacuum from the vacuum tubes and creating a fluid passageway between the blood collection chamber 48 and the vacuum tubes 50. The vacuum tubes 50 quickly fill with blood from the umbilical cord. Because the placenta clamp 74 and the cord restraint 84 provide a firm grip of the umbilical cord, delivery of the placenta is facilitated.

From the foregoing, the present invention provides a device and method of clamping and cutting the umbilical cord and for obtaining an uncontaminated cord blood sample.

It should be appreciated that the apparatus and methods of the present invention are capable of being incorporated in the form of a variety of embodiments, only a few of which have been illustrated and described above. The invention may be embodied in other forms without departing from its essential characteristics. The described embodiments are to be considered in all respects only as illustrative and not restrictive and the scope of the invention is, therefore, indicated by the appended claims rather than by the foregoing description.

What is claimed is:

1. An apparatus for clamping, cutting, and collecting a blood sample from an umbilical cord comprising:

a housing for receiving and entrapping a section of umbilical cord comprising a handle and a lid, wherein the handle and lid are hingedly connected such that the lid may be moved from an open position to a closed position, and wherein the open position allows an umbilical cord to be inserted between the handle and lid;

a clamp releasably connected to the housing for clamping the umbilical cord;

a blade assembly having a sharp blade surface for cutting an entrapped section of umbilical cord, wherein the blade assembly is slidably located in the lid and configured to slide at an angle less than 90° with respect to the blade surface to provide a slicing motion to cut the umbilical cord;

a blood collection chamber located within the handle such that blood from the umbilical cord drains into the blood collection chamber; and a fluid passageway between the blood collection chamber and a blood container.

2. An apparatus as defined in claim 1, further comprising a placenta clamp located in the housing having a surface for gripping the umbilical cord and facilitating delivery of the placenta.

3. An apparatus as defined in claim 2, wherein the placenta clamp is located in the lid.

4. An apparatus as defined in claim 2, wherein the placenta clamp includes ratchet teeth to maintain clamping action of the placenta clamp against the umbilical cord.

5. An apparatus as defined in claim 2, wherein the placenta clamp is configured to slide at an angle less than 90° with respect to the clamp surface.

6. An apparatus as defined in claim 1, further comprising a plurality of projections which are sufficiently sharp to penetrate the umbilical cord and to help retain the umbilical cord within the housing.

7. An apparatus as defined in claim 1, further comprising an absorbent gasket surrounding the blood collection chamber in the handle for collecting and retaining excess blood.

8. An apparatus as defined in claim 1, wherein the blood container is a removable vacuum tube.

9. An apparatus as defined in claim 1, wherein the umbilical cord clamp is a one-piece plastic part.

10. An apparatus as defined in claim 1, wherein the sharp blade surface is stainless steel.

11. An apparatus as defined in claim 1, wherein the sharp blade surface is made of a non-metallic, glass-filled polymeric material.

12. An apparatus as defined in claim 1, wherein the means for releasing the clamp from the housing when the umbilical cord is cut comprises an angled cam affixed to the slidable blade assembly.

13. An apparatus as defined in claim 1, further comprising a safety lock located in the lid for allowing the slidable bade assembly to slide only if the lid is closed.

14. An apparatus as defined in claim 1, wherein the clamp includes a ratchet latch such that the clamp has several locking positions.

15. An apparatus as defined in claim 1, further comprising a clamp hook located on the blade assembly for retaining the clamp to the housing.

16. An apparatus as defined in claim 1, wherein the blood container includes a removable vacuum tube.

17. An apparatus as defined in claim 16, wherein the fluid passageway is closed prior to use and wherein the fluid passageway includes means for opening the passageway and releasing vacuum from the vacuum tube into the blood collection chamber.

18. An apparatus as defined in claim 1, further comprising a sheath configured to hold one or more vacuum tubes and to removably fit within the handle.

19. An apparatus as defined in claim 18, further comprising means for locating the sheath within the handle.

20. An apparatus for clamping, cutting, and collecting a blood sample from an umbilical cord comprising:

a housing for receiving and entrapping a section of umbilical cord comprising a handle and a lid, wherein the handle and lid are hingedly connected such that the lid may be moved from an open position to a closed position, and wherein the open position allows an umbilical cord to be inserted between the handle and lid;

a clamp releasably connected to the housing for clamping the umbilical cord;

a blade assembly having a sharp blade surface for cutting an entrapped section of umbilical cord;

a blood collection chamber located within the handle such that blood from the umbilical cord drains into the blood collection chamber;

a fluid passageway between the blood collection chamber and a blood container; and a placenta clamp located in the housing having a surface for gripping the umbilical cord and facilitating delivery of the placenta.

21. An apparatus for clamping, cutting, and collecting a blood sample from an umbilical cord comprising:

a housing for receiving and entrapping a section of umbilical cord comprising a handle and a lid, wherein the handle and lid are hingedly connected such that the lid may be moved from an open position to a closed position, and wherein the open position allows an umbilical cord to be inserted between the handle and lid;

a clamp releasably connected to the housing for clamping the umbilical cord;

a blade for cutting an entrapped section of umbilical cord slidably located in the lid, wherein the blade is configured to slide at an angle less than 90° with respect to the blade surface to provide a slicing motion to cut the umbilical cord;

means for releasing the clamp from the housing when the umbilical cord is cut;

a blood collection chamber located within the handle for temporarily retaining blood from a cut umbilical cord;

an absorbent gasket surrounding the blood collection chamber in the handle for collecting and retaining excess blood;

a fluid passageway between the blood collection chamber and a removable vacuum tube, wherein the fluid passageway is closed prior to use and wherein the fluid passageway includes means for opening the passageway and releasing vacuum from the vacuum tube into the blood collection chamber; and a placenta clamp located in the housing having a surface for gripping the umbilical cord and facilitating delivery of the placenta.

22. An apparatus as defined in claim 21, wherein the placenta clamp is located in the lid.

23. An apparatus as defined in claim 21, wherein the placenta clamp includes ratchet teeth to maintain clamping action of the placenta clamp against the umbilical cord.

24. An apparatus as defined in claim 21, wherein the placenta clamp is configured to slide at an angle less than 90° with respect to the clamp surface.

25. An apparatus as defined in claim 21, further comprising a plurality of projections which are sufficiently sharp to penetrate the umbilical cord and to help retain the umbilical cord within the housing.

26. An apparatus as defined in claim 21, wherein the clamp is a one-piece plastic part.

27. An apparatus as defined in claim 21, wherein the blade is stainless steel.

28. An apparatus as defined in claim 21, wherein the blade is made of a non-metallic, glass-filled polymeric material.

29. An apparatus for clamping, cutting, and collecting a blood sample from an umbilical cord comprising:

a housing for receiving and entrapping a section of umbilical cord comprising a handle and a lid, wherein the handle and lid are hingedly connected such that the lid may be moved from an open position to a closed position, and wherein the open position allows an umbilical cord to be inserted between the handle and lid;

a clamp releasably connected to the housing for clamping the umbilical cord, wherein the clamp is a one-piece molded plastic part;

a blade assembly having a sharp blade surface for cutting an entrapped section of umbilical cord, wherein the blade assembly is slidably located in the lid and configured to slide at an angle less than 90° with respect to the blade surface to provide a slicing motion to cut the umbilical cord;

a clamp hook located on the blade assembly for retaining the clamp to the housing;

means for releasing the clamp from the housing when the umbilical cord is cut comprising an angled cam affixed to the slidable blade assembly;

a blood collection chamber located within the handle for temporarily retaining blood from a cut umbilical cord;

an absorbent gasket surrounding the blood collection chamber in the handle for collecting and retaining excess blood;

a sheath configured to hold one or more vacuum tubes and to removably fit within the handle, said sheath having means for locating the sheath within the handle;

a fluid passageway between the blood collection chamber and the vacuum tubes, wherein the fluid passageway is closed prior to use and wherein the fluid passageway includes means for opening the passageway and releasing vacuum from the vacuum tubes into the blood collection chamber;

a placenta clamp located in the lid having a surface for gripping the umbilical cord and facilitating delivery of the placenta, wherein the placenta clamp includes ratchet teeth to maintain clamping action of the placenta clamp against the umbilical cord, and wherein the placenta clamp is configured to slide at an angle less than 90° with respect to the clamp surface; and a plurality of projections affixed to the lid which are sufficiently sharp to penetrate the umbilical cord and to help retain the umbilical cord within the housing.

30. An apparatus as defined in claim 29, wherein the sharp blade surface is stainless steel.

31. An apparatus as defined in claim 29, wherein the sharp blade surface is made of a non-metallic, glass-filled polymeric material.

* * * * *